United States Patent
Baust et al.

(10) Patent No.: US 9,213,025 B2
(45) Date of Patent: Dec. 15, 2015

(54) TISSUE ENGINEERED MODEL

(71) Applicant: CPSI HOLDINGS LLC, Owego, NY (US)

(72) Inventors: John G. Baust, Candor, NY (US); Joshua T. Smith, Owego, NY (US); Kimberly L. Santucci, Apalachin, NY (US); Kristi K. Snyder, Candor, NY (US); Anthony T. Robilotto, Binghamton, NY (US); Robert G. Van Buskirk, Apalachin, NY (US); John M. Baust, Owego, NY (US); William L. Corwin, Johnson City, NY (US); Jennie F. McKain, Endicott, NY (US)

(73) Assignee: CPSI Holdings LLC, Owego, NY (US)

( * ) Notice: Subject to any disclaimer, the term of this patent is extended or adjusted under 35 U.S.C. 154(b) by 0 days.

(21) Appl. No.: 14/206,533

(22) Filed: Mar. 12, 2014

(65) Prior Publication Data
US 2014/0273063 A1 Sep. 18, 2014

Related U.S. Application Data

(60) Provisional application No. 61/779,468, filed on Mar. 13, 2013.

(51) Int. Cl.
*C12N 5/00* (2006.01)
*G01N 33/50* (2006.01)

(52) U.S. Cl.
CPC ........ *G01N 33/5008* (2013.01); *G01N 33/5017* (2013.01)

(58) Field of Classification Search
CPC .................................................... C12N 5/0062
See application file for complete search history.

(56) References Cited

PUBLICATIONS

Derda et al., "Paper-supported 3D cell culture for tissue-based bioassays," Proc Natl Acad Sci USA 106(44):18457-18462, 2009.*

* cited by examiner

*Primary Examiner* — Rosanne Kosson
(74) *Attorney, Agent, or Firm* — Hoffman Warnick LLC (57) ABSTRACT

A tissue engineered model (TEM) structure, an apparatus and method for making a TEM structure, and methods of using a TEM structure are disclosed. In an embodiment, the TEM structure includes at least one TEM segment. Each TEM segment includes a frame defining a bounded area, the frame having a height, a first edge, and a second edge opposite the first edge, each of the first edge and the second edge defining a perimeter of the bounded area, and the height defining a distance between the first edge and the second edge; a membrane affixed to the first edge about a perimeter of the frame; and a solidified gel and cell matrix disposed within the bounded area within the frame, wherein the solidified gel and cell matrix substantially fills a volume defined by the bounded area and the height of the frame.

16 Claims, 11 Drawing Sheets

TISSUE ENGINEERED MODEL

CROSS REFERENCE TO RELATED APPLICATION

The present application claims the benefit of U.S. Provisional Application Ser. No. 61/779,468, filed Mar. 13, 2013, the entirety of which is incorporated herein.

FIELD OF THE INVENTION

The present invention relates generally to laboratory based research, and, in particular, to tissue engineered models for pre-clinical animal studies.

BACKGROUND OF THE INVENTION

The increased use of laboratory based cellular systems in basic research and pharmaceutical discovery has led to a greater need for in vivo animal studies. As a result, studies have demanded longer time periods for the actual studies which, in turn, leads to higher costs and often results in a disconnect between the in vitro and in vivo data.

Tissue engineering, as introduced in the mid-1980s, has been described as the use of a combination of cells, engineering and materials methods, to improve or replace biological functions. While it was once categorized as a sub-field of biomaterials, it has grown in scope to include suitable biochemical and physiochemical factors to improve or replace biological functions.

Progress in the past decade has enhanced understanding of the structure-function relationships in living organisms. These developments have yielded a set of tissue replacement parts and implementation strategies. Scientific advances in biomaterials, stem cells, biomimetic environments, growth, and differentiation factors have created opportunities to fabricate tissues in the laboratory from combinations of engineered extracellular matrices or scaffolds, cells, and biologically active molecules.

Despite the advances, numerous challenges and fundamental questions remain about how cells work within engineered matrices, thus limiting the utility of the initially designed engineered tissue products. In many cases, creation of functional tissues and biological structures in vitro requires extensive culturing to promote survival, growth and inducement of functionality. In general, cells require maintenance of growth conditions in culture including control of oxygen levels, pH, humidity, temperature, nutrients and osmotic pressure. Tissue engineered cultures, however, present additional problems in maintaining culture conditions. In standard cell culture, diffusion is often the sole means of nutrient and metabolite transport. As a culture grows, such as the case with engineered organs and whole tissues, other mechanisms must be employed to maintain the culture, such as the creation of capillary networks within the tissue.

Another issue with tissue culture is introducing the proper factors or stimuli required to induce functionality. In many cases, simple maintenance culture is not sufficient. Growth factors, hormones, specific metabolites or nutrients, and chemical and physical stimuli are sometimes required. For example, certain cells such as chondrocytes, respond to changes in oxygen tension as part of their normal development. Others, such as endothelial cells, respond to shear stress from fluid flow by blood vessels. Mechanical stimuli, such as pressure pulses seem to benefit various cardiovascular tissues including heart valves, blood vessels, or pericardium.

Further challenges include implementing a more complex functionality in a tissue model, as well as both functional and biomechanical stability in laboratory-gown tissues destined for replacement of tissues needed for animal and human research. As increased costs in clinical research associated with medical care continue to grow exponentially; improved research methods and innovation in tissue engineered modeling will desirably reduce costs while improving deliverable treatment options.

SUMMARY OF THE INVENTION

In a first aspect, a tissue engineered model (TEM) structure is provided. The TEM structure comprises at least one TEM segment, each TEM segment including: a frame defining a bounded area, the frame having a height, a first edge, and a second edge opposite the first edge, each of the first edge and the second edge defining a perimeter of the bounded area, and the height defining a distance between the first edge and the second edge; a membrane affixed to the first edge about the perimeter of the frame; and a solidified gel and cell matrix disposed within the bounded area, wherein the solidified gel and cell matrix substantially fills a volume defined by the bounded area and the height of the frame.

In a second aspect, a method is provided for constructing a tissue engineered model (TEM) structure. The method comprises forming a TEM segment, the forming including: providing a frame defining a bounded area, the frame including a height, a first edge, and a second edge opposite the first edge, each of the first edge and the second edge defining a perimeter of the bounded area, and the height defining a distance between the first edge and the second edge, and a membrane affixed to the first edge about the perimeter of the frame; orienting the frame such that the second edge faces upward; pouring a liquid matrix precursor solution into a volume within the frame defined by the bounded area and the height of the frame, wherein the liquid matrix precursor solution includes a gelling agent and is seeded with selected cells; solidifying the liquid matrix precursor solution to form a matrix; and growing the cells in culture.

In a third aspect, an apparatus is provided for constructing a tissue engineered model (TEM) structure. The apparatus comprises a scaffold, a scaffold container for containing the scaffold within a fluid medium, and at least one riser disposed between the first plate of the scaffold and a bottom surface of the scaffold container for providing fluid circulation through the hole in the first plate. The scaffold includes a first plate having a hole therein; and a plurality of post members each having substantially the same length, each of the post members extending from a first face of the first plate in a direction substantially perpendicular relative to the first plate.

These and other aspects, advantages and salient features of the invention will become apparent from the following detailed description, which, when taken in conjunction with the annexed drawings, disclose embodiments of the invention.

It is noted that the drawings of the disclosure are not necessarily to scale. The drawings are intended to depict only typical aspects of the disclosure, and therefore should not be considered as limiting the scope of the disclosure. In the drawings, like numbering represents like elements between the drawings.

DETAILED DESCRIPTION

Turning to the drawings, FIGS. 1-19 provide various embodiments of a tissue engineered model (TEM) structure and method for using the same. The TEM structure provides a tool for complex in vitro type studies while providing a culture state more similar to and compatible with that found in an in vivo setting. The TEM structure further provides for an off-the-shelf living tissue model tool for use in early and mid-stage drug discovery development studies, bridging the gap between two dimensional (2D) in vitro culture and in vivo animal studies while reducing the cost and increasing consistency and reproducibility of discovery science endeavors.

Figure 1:
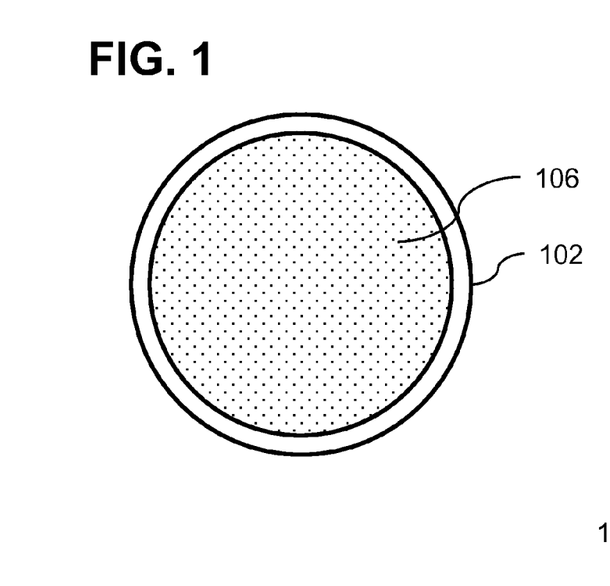
FIGS. 1 and 2 depict a top view and a perspective view, respectively, of a frame 102 in accordance with an embodiment of the invention.
Figure 2:
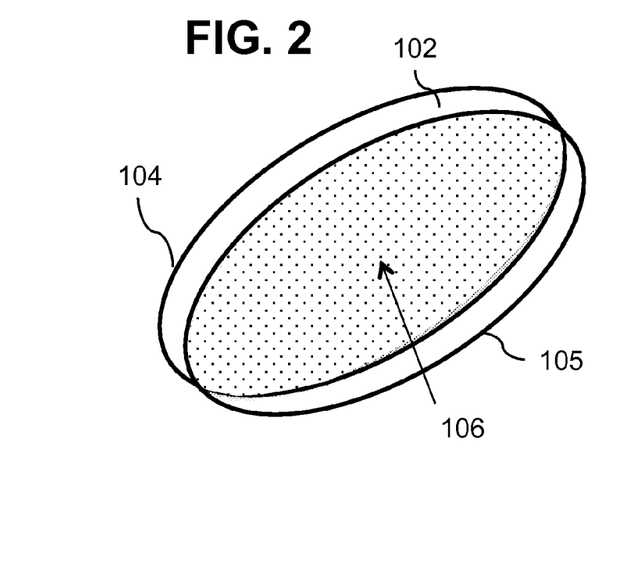
Figure 3:
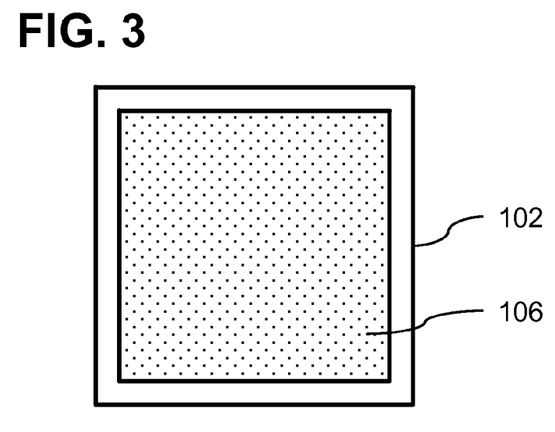
FIGS. 3-5 depict top views of frames 102 in accordance with further embodiments of the invention.
Figure 4:
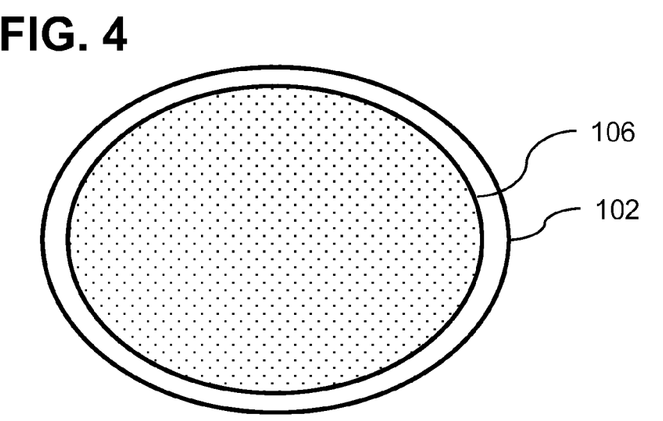
Figure 5:
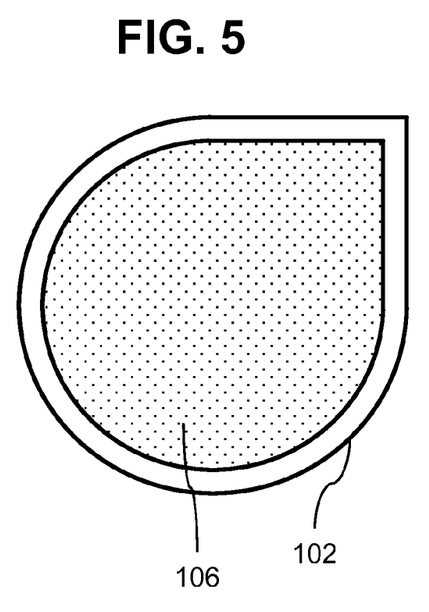
Figure 12:
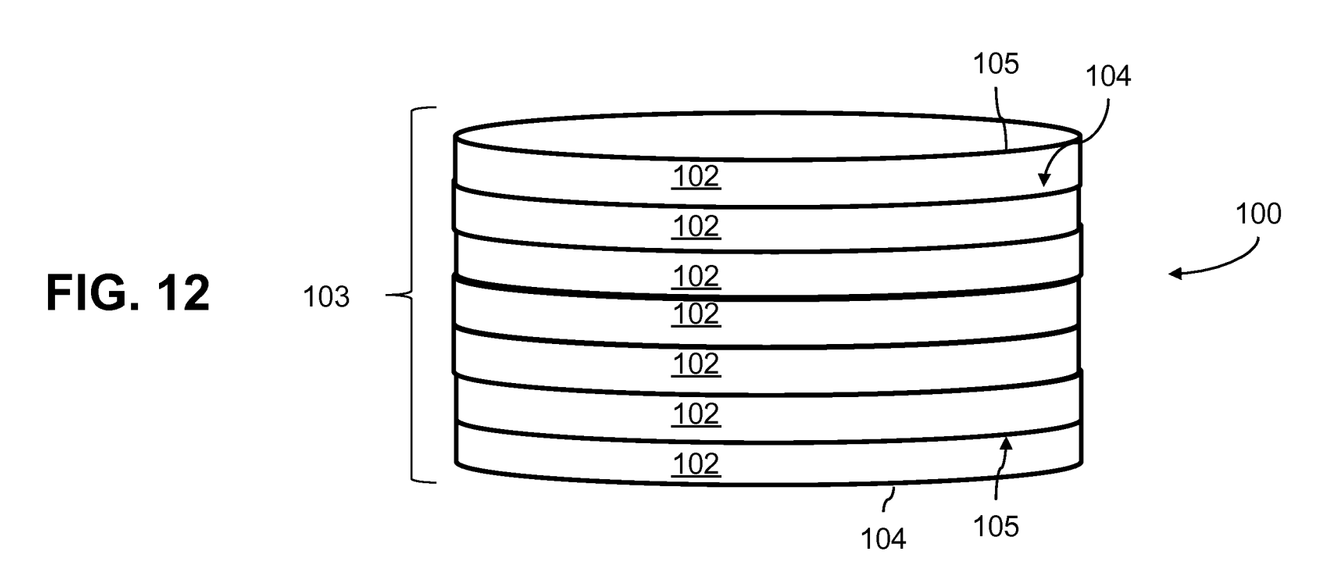
FIG. 12 illustrates an embodiment of tissue engineered model (TEM) structure 100.

FIGS. 1-7 illustrate a frame 102 which may be used to form TEM structure 100 (FIG. 12). Each individual frame 102 may be, e.g., about 2-8 mm thick and about 2-5 cm across. As best shown in FIGS. 2 and 8, each frame 102 includes a substantially vertical band with a first edge 104 to which a membrane 106 is affixed, and a second edge 105 opposite the first edge. Frame 102 may have a height of, e.g., about 2-8 mm, such that first edge 104 and second edge 105 are about 2-8 mm apart. In the methods described further below, frame 102 may be oriented such that first edge 104 may be a bottom edge, and second edge 105 may be a top edge. In some embodiments, such as shown in, e.g., FIGS. 1-2, frame 102 may be substantially annular or ring shaped. In other embodiments, however, such as shown in FIGS. 3-5, frame 102 may be any regular or irregular geometric shape. For example, frame 102 may be substantially square or rectangular (FIG. 3), ovoid (FIG. 4), or other geometric shaped, or frame 102 may be shaped to approximate the shape of a particular organ or tissue (FIG. 5).

Figure 6:
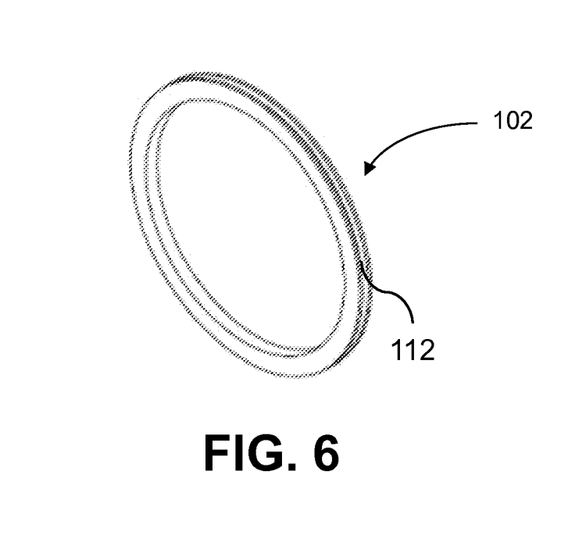
FIGS. 6 and 7 illustrate perspective and side views, respectively, of an embodiment of a frame 102.
Figure 7:
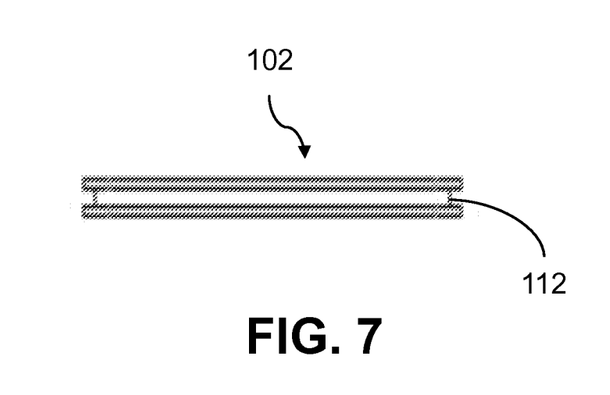
Figure 8:
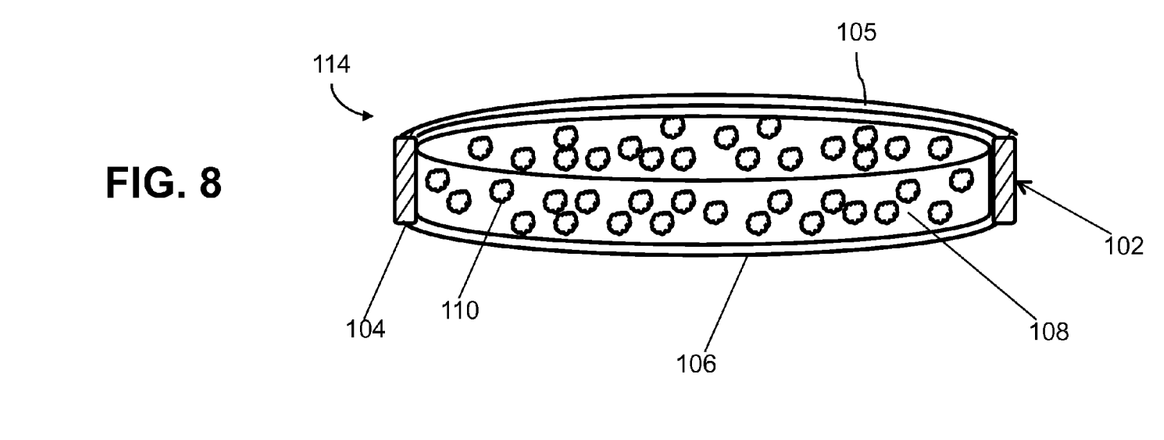
FIGS. 8-10 illustrate transparent cross-sectional views of embodiments of the invention.

In some embodiments, shown in FIGS. 6-7, frame 102 may further include a groove 112 along its radially outward-facing surface for accommodating an o-ring. The o-ring may be used to affix membrane 106 to frame 102 by sliding the o-ring into groove 112 and retaining an edge of membrane 106 within groove 112, between groove 112 and the o-ring. In various other embodiments, an adhesive on edge 104 (FIG. 8) may be utilized to affix membrane 106 to the first edge 104 of frame 102. In further embodiments, membrane 106 may be heat fused, or affixed by any other method known in the art, to first edge 104 of frame 102.

Figure 9:
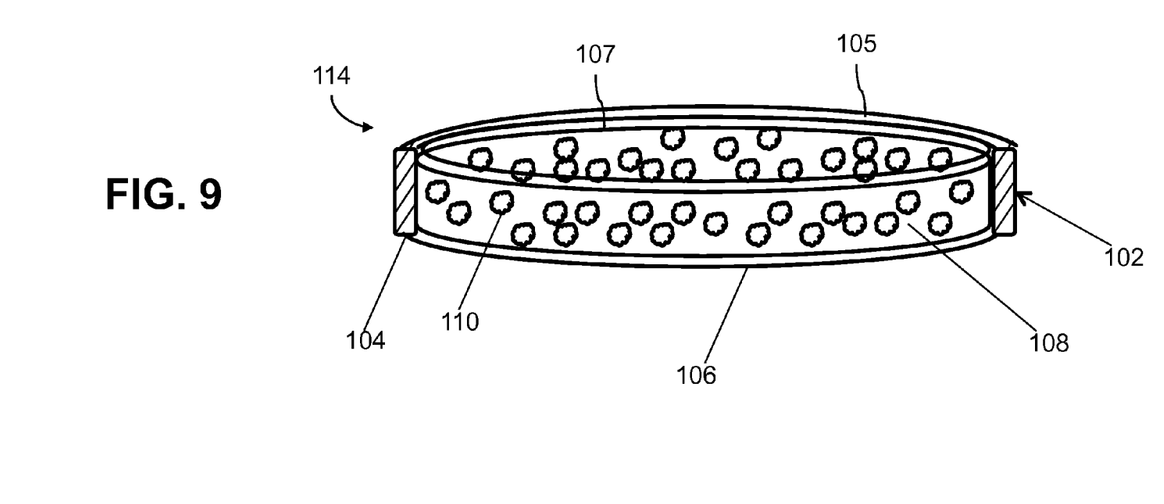

In some embodiments, as shown in FIGS. 2 and 8, second edge 105 does not have a membrane attached, whereas in other embodiments, as shown in FIG. 9, first membrane 106 may be adhered to first edge 104, and a second membrane 107 maybe affixed to second edge 105 of frame 102. In such an embodiment, gel 108/cell 110 matrix is sandwiched between first and second membranes 106 and 107. Membrane 106, and where present, membrane 107 may promote retention and/or attachment of the gel 108/cell 110 matrix within frame 102 (FIG. 8) as described further below.

As shown, gel matrix 108 may include cells 110 incorporated therein. Gel 108/cell 110 matrix may be formed by mixing any number of culture media or salt solutions with a gelling agent, such as, e.g., collagen, matrigel, gelatin, agarose, fibronectin, engineered scaffolds, polymer based gels, hydrogels, or any other gel forming agent, alone or in combination, to form the liquid gel matrix precursor solution. Cells 110 of any type are added to the solution to create a specific tissue type model. For example, cancerous prostate, renal, breast, pancreatic, liver, lung, or skin cells may be added to gels, separately, create a 3D TEM of each respective cancer. Normal cells, such as cardiomyocyte, endothelial, epithelial, smooth muscle, stem cells, etc., can be utilized to create normal (non-diseased) models as well. In other embodiments, combinations or mixtures of cells may be added to create a heterogeneous tissue model reflecting the native cell constituents of a complex tissue. The mixtures are then poured into frames 102, and allowed to solidify under appropriate conditions, i.e., in a cell culture incubator, at room temperature in a sterile tissue culture hood, etc.

Figures 10, 11:
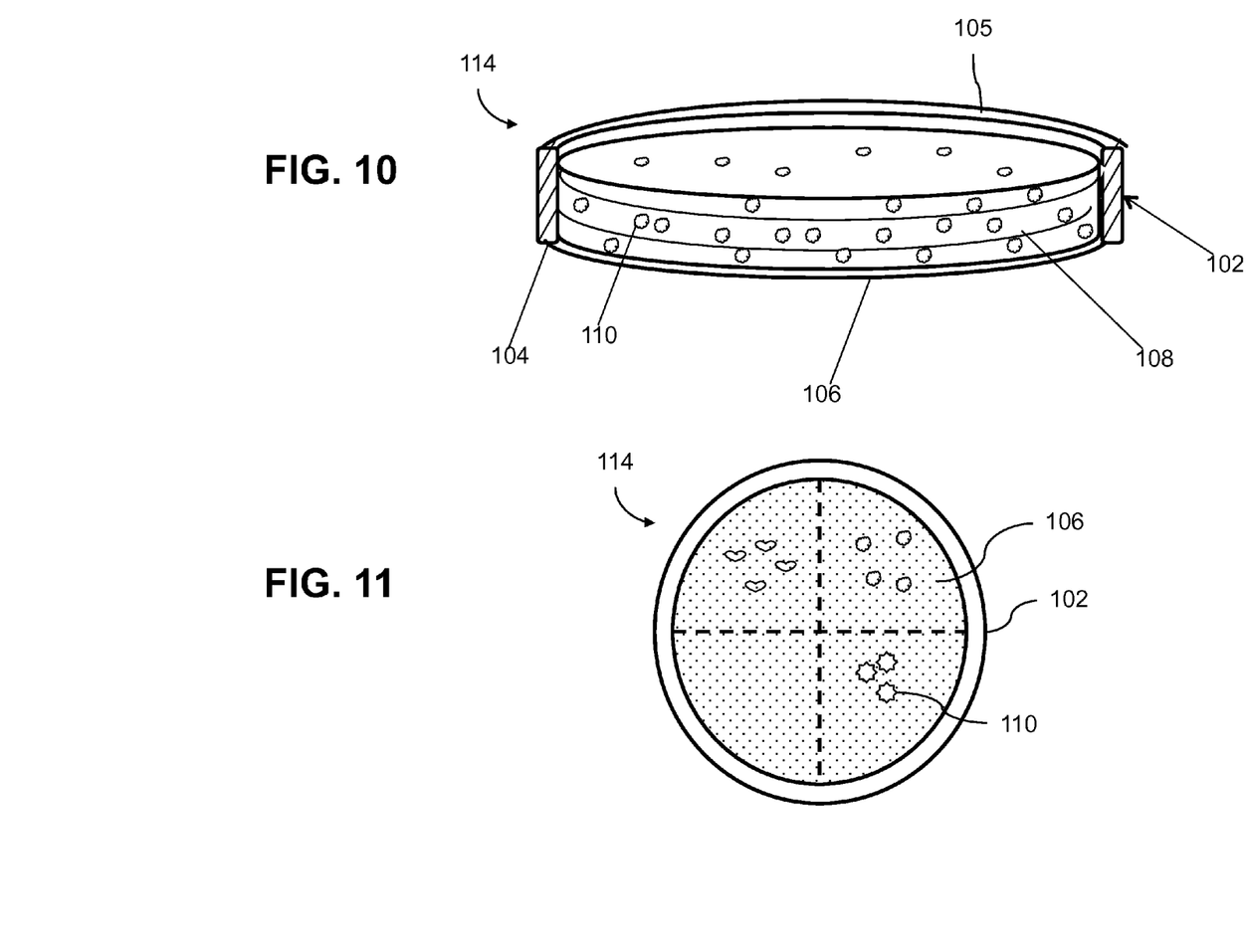
FIG. 11 illustrates a top view of a TEM segment 114 in accordance with an embodiment of the invention.

As noted, in some embodiments, gel 108/cell 110 matrix may be homogenous with respect to cell type, whereas in other embodiments, gel 108/cell 110 matrix may include a heterogeneous mixture of cell types. In further embodiments, as shown in FIG. 10, multiple individual layers of liquid gel matrix precursor solution containing homogenous cells or a heterogeneous cell mixture may be poured into frame 102, creating a layered TEM segment 114 within an individual frame 102. In other embodiments, as shown in FIG. 11, frame 102 may be divided into segments or sections, and individual mixtures of cells 110 can applied into each section within frame 102 thereby creating distinct regions of cell populations within an individual TEM 114. For example, the TEM segment 114 shown in FIG. 11 is divided approximately into quadrants, with different cell 110 types in each quadrant. It is noted that this is merely one exemplary embodiment; each quadrant (or other fractional division of TEM 114) could contain either heterogeneous or homogenous cells.

Once solidified, individual TEM segments 114, shown in FIGS. 8-11, include a gel 108/cell 110 matrix disposed within the area and volume defined by frame 102, membrane 106, and where present, membrane 107 (FIG. 9). TEM segments 114 may then be placed into a culture container such as a Petri dish, submerged in media and placed in culture to allow for cell population adhesion, growth, and communication. The TEM segments 114 are typically allowed to culture for one to two days, or as desired, prior to utilization in experimentation.

In various embodiments, first and second membrane 106, 107 may be any type of membrane structure, but in some exemplary embodiments may be an optically clear, biologically active (protein or treated/coated), microporous membrane. In some embodiments, first and/or second membranes 106, 107 may each be a sheet of cellulose. The use of such an optically clear, biologically active, microporous membrane 106, 107 allows for the attachment and solidification of the cell 110/gel matrix 108 while allowing for nutrient and gas diffusion from both the top and bottom of 3D TEM structure 100 (FIG. 12). Further, an optically clear membrane 106, 107 may allow for in situ real-time visualization of the culture via microscopy (both phase contrast and fluorescence).

FIG. 12 depicts a three dimensional (3D) TEM structure 100. TEM structure 100 may include a series of individual TEM structures 114, each as shown in FIGS. 8-11, that are vertically stacked and substantially laterally aligned with one another in a stack 103. When TEM segments 114 are arranged in a stack 103, TEM segments 114 may be oriented such that first edge 104 is on an underside or bottom of each frame 102, and abuts a second edge 105 of an adjacent TEM segment 114. Any number of TEM segments 114 may be vertically assembled in stack 103. As depicted in FIG. 12, for example, seven TEM segments 114 containing layers of cell 110/gel matrix 108 have been assembled into stack 103. Other numbers of TEM segments 114 may also be used. For example, in another embodiment, about 10-15 TEM segments 114 containing prostate cancer cells may be used to create a substantially continuous 3D prostate tumor model of about 4 cm in diameter by 3-4 cm in height, which may then be used for experimentation. Collectively, stack 103 of TEM segments 114 forms TEM structure 100 (FIG. 12). In various embodiments, the TEM segments 114 making up stack 103 may or may not have the same shape as shown in FIGS. 1 and 3-5).

Figure 13:
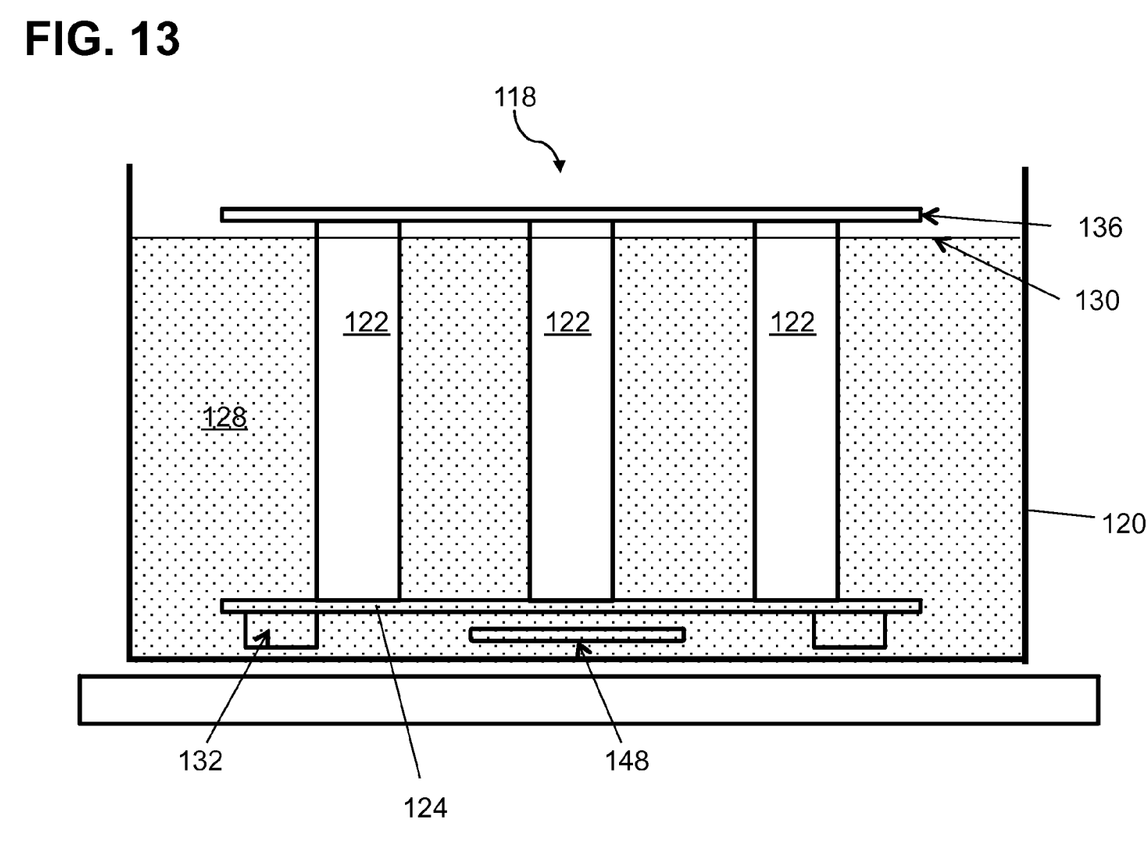
FIG. 13 illustrates a scaffold in a scaffold container in accordance with an embodiment of the invention.
Figure 14:
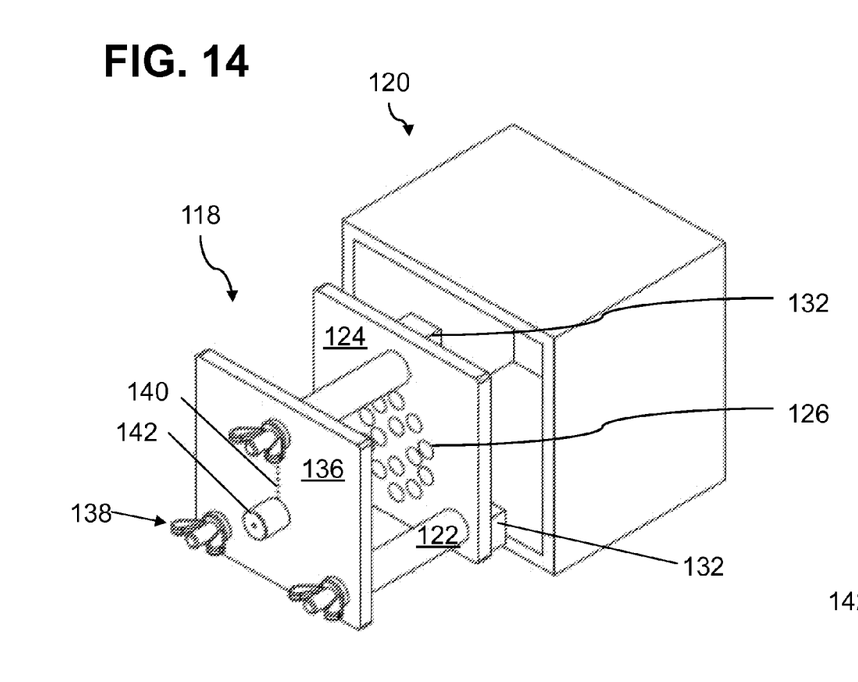
FIGS. 14-16 illustrate aspects of scaffold container for creation and use of the tissue TEM structure 100 of FIG. 12 in accordance with embodiments of the invention.
Figure 16:
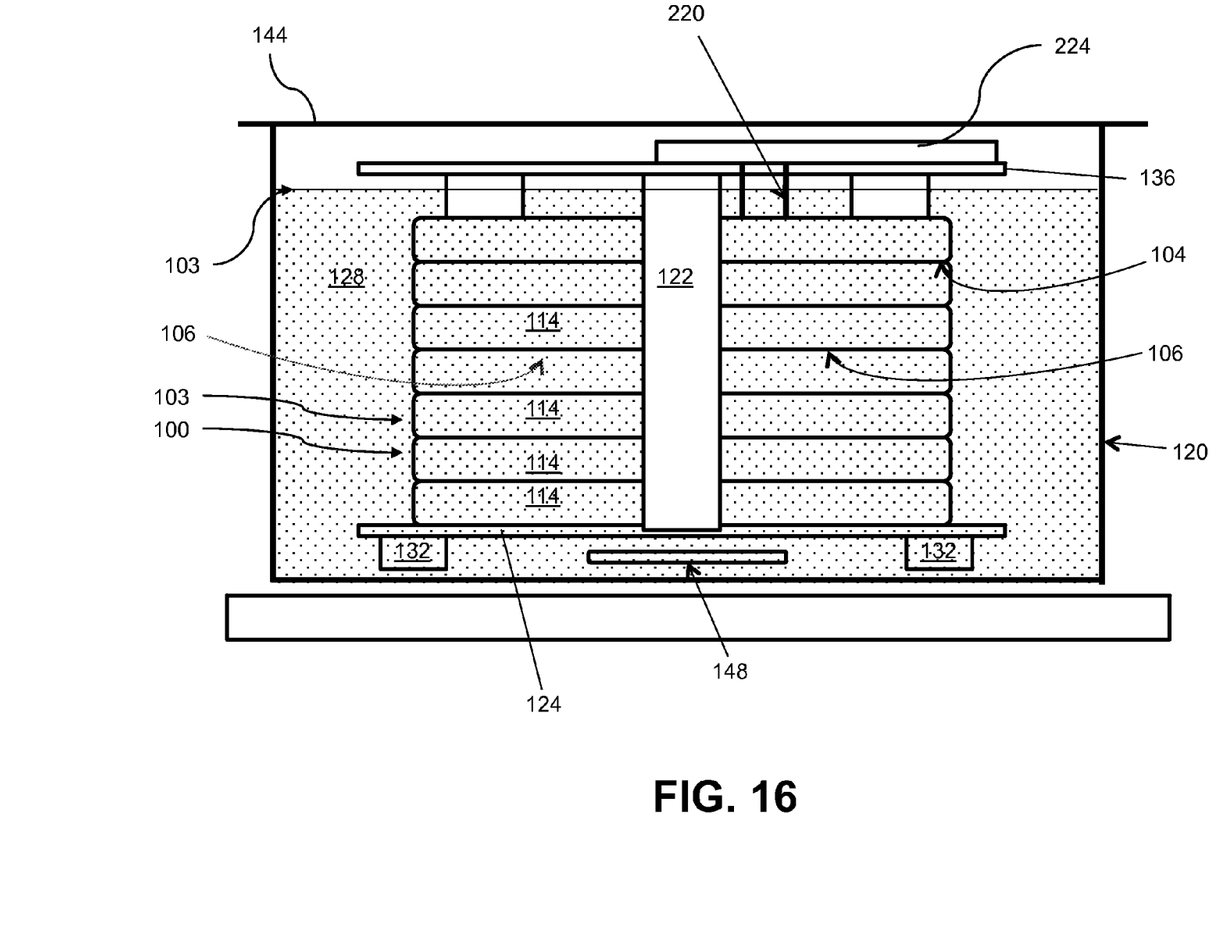

As shown in FIGS. 13-14, a scaffold apparatus 118, which may be placed in scaffold container 120, may be provided for ease of positioning TEM segments 114 in a stack 103 as shown in, e.g., FIG. 12. Scaffold apparatus 118 may include a number of positioning posts 122, which extend vertically and substantially perpendicularly relative to bottom plate 124, to which they are affixed at one end. In the embodiment shown in FIG. 13, three positioning posts or rods 122 are provided, however, other numbers of posts 122 may be provided in other embodiments for assisting in the alignment of TEM segments 114 in stack 103 (FIG. 16). Positioning posts 122 may be of any size, shape, or configuration, depending on the shape, size, and other features of the desired TEM structure 100 (FIG. 12) and the individual TEM segments 114. As shown in FIG. 16, TEM segments 114 may be placed on scaffold apparatus 118, forming an aligned stack 103.

With reference to FIGS. 14 and 16, bottom plate 124 may include a plurality of holes 126 (FIG. 14) therein. A plurality of risers 132 may further be provided, resting on a bottom surface of scaffold container 120, supporting bottom plate 124 of scaffold 118 such that bottom plate 124 does not rest on the bottom of scaffold container 120. In some embodiments, two or three risers 132 may be provided. Together, holes 126 and risers 132 facilitate circulation of media/nutrients 128 (FIG. 16) through scaffold container 120 and TEM structure 100 (FIG. 16). Media/nutrients 128 fill scaffold apparatus container 120 up to media level 130, submerging TEM structure 100.

Figure 15:
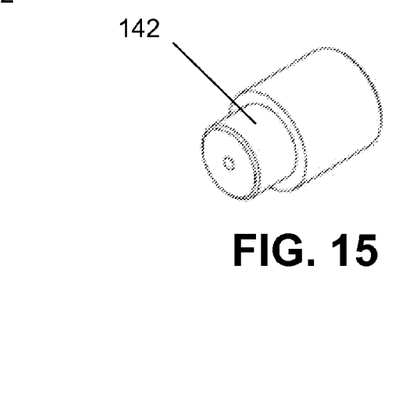

With continued reference to FIGS. 14-16, once a stack 103 of TEM segments 114 is formed to the desired size of TEM structure 100, stack 103 may be held in place within scaffold 118 by top plate 136.

Top plate 136 may be secured to positioning posts 122 by fasteners 138 as shown in FIG. 14, which may particularly be threaded fasteners such as, e.g., threaded mandrels, wing nuts, or threaded screws, or by plastic dowel adhesives or other fasteners as known in the art. Top plate 136 may include a plurality of holes 140 (FIG. 14) to facilitate flow of media/nutrients 128 (FIG. 16) through stack 103 when the apparatus is assembled and placed in container 120 as shown in FIG. 16. Holes 140 in top plate 136 further permit the insertion of one or more devices into TEM structure 100 such as, e.g., monitoring probes.

In some embodiments, permeable or impermeable tubes may also be inserted into stack 103 during assembly to allow for direct media flow through TEM structure 100 to simulate the impact of vascular circulation within TEM structure 100. The tubes may be, e.g., synthetic tubing or cellular-based vessels created using, e.g., endothelial, smooth muscle cells in combination with directed continuous or pulsatile media flow through TEM structure 100. Tubes may be used in particular in drug diffusion studies or in ablation studies using a heating or cooling source. Permeable tubes may be used for cell migration studies, such as cancer cell or immune cell migration, to model and study the impact of, e.g., cell migration, circulation rate, drug, and other therapy interactions.

Additionally, as shown in FIGS. 14-15, a needle adapter 142 may be provided within top plate 136, to facilitate the introduction of drugs, chemicals, cells, and/or medical probes directly into TEM stack 103 when assembled (FIG. 14). Needle adapter 142 is shown in greater detail in FIG. 15.

Scaffold container 120 may be a seal-tight container of any size, shape, and dimension, in which the assembled TEM stack 103 may be positioned and maintained under optimal growth conditions. Lid 144 may provide the seal, although lid 144 may include a series of access ports therein to allow introduction of drugs, chemicals, cells, and/or medical probes directly or indirectly into TEM structure 100. Container 120 is filled as noted above with media/nutrients 128 as shown in FIG. 16, creating a nutrient/media bath in which TEM structure 100 is submerged. Container 120 may include any number of controllable and adjustable features such as temperature monitoring and maintenance devices, circulating pumps, stir bars 148 (FIG. 16) or a stir plate, pressure and/or flow sensors, pH meters or monitors, and any desirable laboratory tool which can monitor and record various parameters in real-time via either integrated or satellite computer systems. TEM structure 100 may remain within container 120 for the duration of experimentation as understood in the art.

Once experimentation is complete, TEM structure 100 may be removed from scaffold 118. It is noted that TEM segments 114 in stack 103 are detachably assembled to one another, such that stack 103 can be disassembled and assembled at various stages of research. Therefore, the cell 110/gel 108 matrix within each TEM segment 114 can be vertically assembled and disassembled and manipulated either as single TEM segments 114 serving as slices of a stack 103, or as an integral 3D TEM structure 100. TEM structure 100 may be placed into culture, storage or disassembled into individual TEM segments 114, readily separating TEM structure 100 into individual gel 108/cell 110 matrix layers. TEM segment 114, which may contain cells therein may then returned to culture or analyzed via microscopy fluorescence imaging or any other type of cell or molecular analyses. Such analyses may include matrix digestion and cell extraction for flow cytometry, RNA, DNA, or protein isolation and analysis. Any number of other analyses may also be performed as desired. Staining of individual gel 108/cell 110 matrix layers derived from TEM segments 114 may also be implemented for visualization of cells 110 or matrix materials. Other additions or combinations may be useful in affecting the characterization and analytical aspects of the invention.

As noted, scaffold apparatus 118 and scaffold container 120 also provide an environment suitable for use of TEM structure 100 for research purposes. TEM structure 100 as described above may have a variety of research uses and applications in various embodiments. For example, a shown in FIGS. 17-19, cell and tissue behavior can be assessed in real-time over the entire thermal gradient of an ablation zone, drug exposure, or cell of gene therapy.

Figure 17:
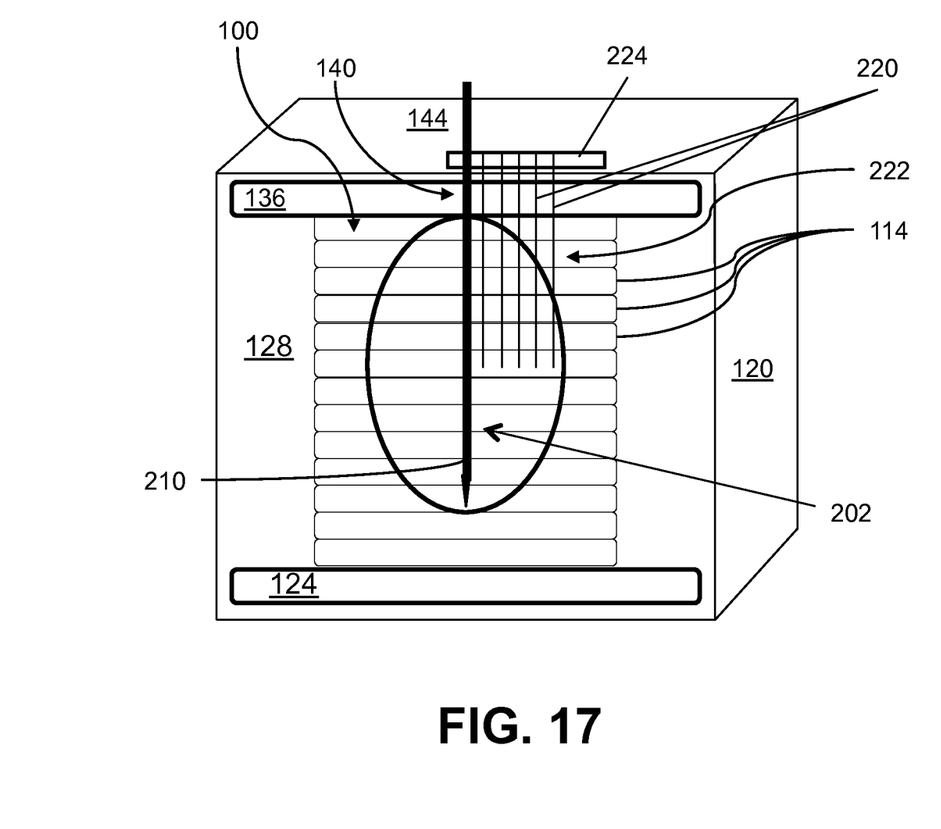
FIGS. 17-19 illustrate examples of uses of the TEM structure of FIG. 12 in accordance with embodiments of the invention.

FIG. 17 shows TEM structure 100 disposed in scaffold 118 (FIG. 16) and within scaffold container 120 similar to the depiction of FIG. 16. A thermal ablation device 210, which may be, e.g., a cryoprobe, is inserted through an access port in lid 144 and through needle adaptor 142 (FIGS. 14-15) and hole 140 (FIG. 14) in top plate 136, into a test area or lesion 202 in TEM structure 100. As shown in FIG. 14, needle adaptor 142 may be inserted through hole 140 in top plate 136, and may be sized to accommodate a particular thermal ablation device 210.

In such an embodiment, TEM structure 100 may be a solid tissue model of a tumor or organ. Monitoring probes 220 (FIGS. 16-17) may similarly be inserted through holes 140 in top plate 136, such that a distal end of each monitoring probe 220 is inserted into TEM structure 100, and a proximal end of each monitoring probe 220 is connected with a probe monitoring fixture 224, which performs data acquisition and monitoring via monitoring probes 220. In some embodiments, as shown in FIG. 17, a plurality of monitoring probes 220 may be provided in the form of an array 222. As thermal ablation device 210 is operated in TEM structure 100, monitoring probes 220 may gather a variety of types of data. Where monitoring probes 220 are thermocouples, for example, they may gather temperature data at a variety of radial distances and depths relative to thermal ablation device 210 to provide thermal profile information over time, which may be useful in evaluating, e.g., the results or performance of a procedure or device. In other embodiments, other parameters may be evaluated by monitoring probes 220, including, e.g., rate and distance of drug diffusion from a site.

Figure 18:
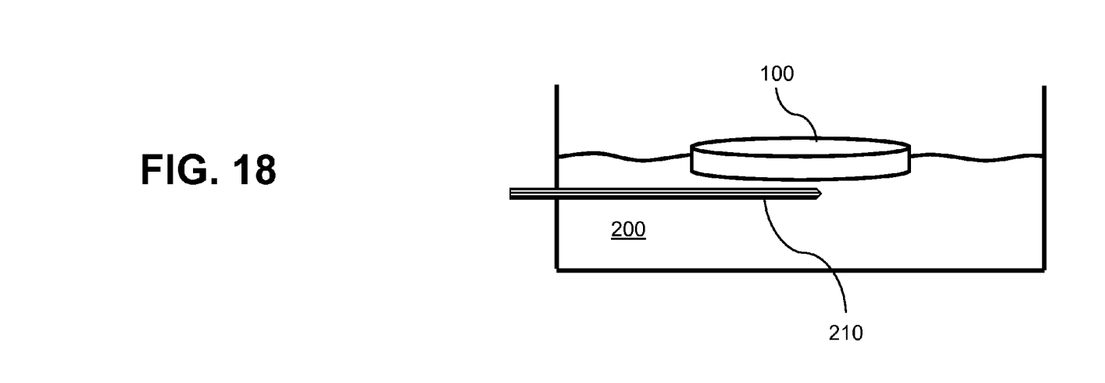
Figure 19:
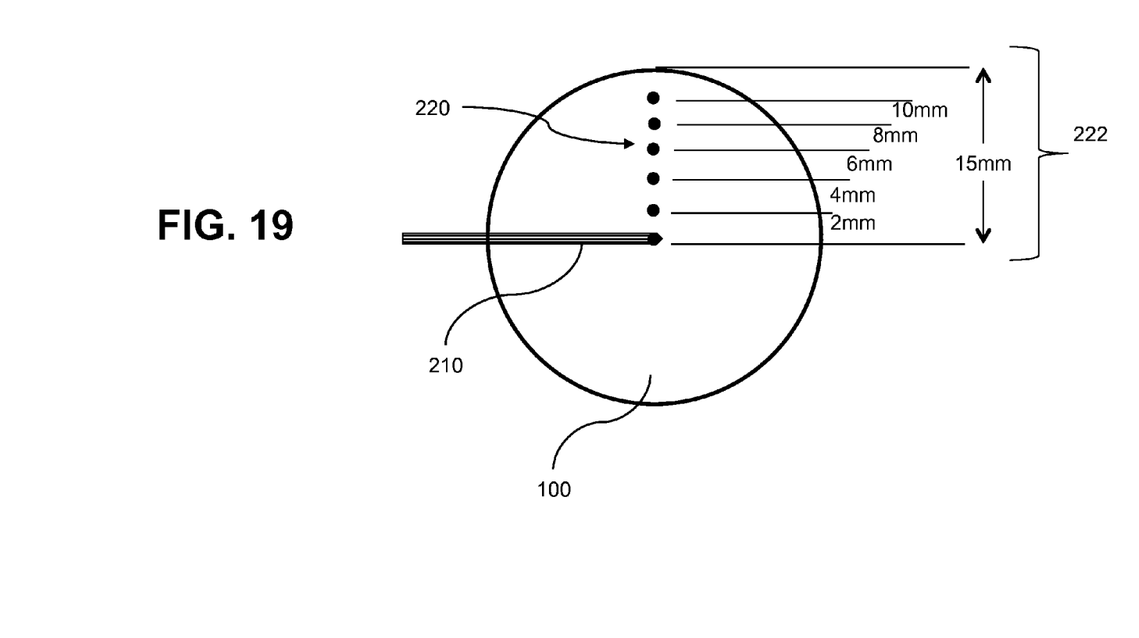

In an example of a use outside of scaffold container 120, FIGS. 18-19 show a TEM structure 100, which may either be a TEM segment 114 (FIG. 8) or a stack 103 of TEM segments 114 (FIG. 12) floating in a warm bath 200. Warm bath 200 may simulate, e.g., heat load on cardiac tissue in the body. A thermal ablation device 210 may be positioned in bath 200 beneath TEM structure 100, with a tip approximately beneath a center of TEM structure 100. As shown in FIG. 19, monitoring probes 220, which may be in the form of an array 222, may be used to monitor temperature in TEM structure 100 during operation of thermal ablation device 210. In the embodiment shown in FIG. 19, each of the monitoring probes 220 is spaced approximately 2 mm apart from the next monitoring probe 220, extending radially outward from the center of TEM structure 100, however any appropriate or desired spacing may also be used, and may vary with the size of the area subjected to, e.g., a temperature gradient. The radially inner-most monitoring probe 220 may be disposed approximately directly vertical relative to the tip of thermal ablation device 210. In some embodiments, monitoring probes 220 may be thermocouples as previously noted.

During operation of thermal ablation device 210, monitoring probes 220 may collect tissue temperature data over time at varying radial distances from the tip of thermal ablation device 210. This data may be used to evaluate various parameters, such as time to reach a temperature at which cell death is achieved, temperature gradients within types of tissues, spatial distances between points of different temperatures, and other measures of procedure and device effectiveness.

The foregoing are merely two possible examples of uses of TEM structure 100. They are not intended to be limiting, but rather, examples of how TEM structure 100 may be used. TEM structure 100 facilitates the study of the effects of various drugs, ablative therapies, compound diffusion characteristics, and basic discovery science, as desired. The resulting tissue-like structure in TEM structure 100 realistically models the architecture and differentiated function of human tissues, and allows integration with the formation of microstructures. TEM structure 100 allows for more complex cell-cell/matrix interactions, vascular simulations, multiple cell types, and the formation of lesions with the ease of assessment typically associated with 2D cultures. TEM structure 100 provides greater insight into molecular based responses of cells and tissues in numerous settings.

This allows a more complete view of corresponding cellular responses as compared to that in either animal models or monolayer cultures. Studies confirm successful use of TEM for preliminary identification of drugs and gene targets. In addition, TEM structure 100 provides the benefit of selective sensitization of cells to freezing. The model provides a basic research tool that allows for a more thorough understanding of stress initiated death such as apoptosis and necrosis, as well as other cellular response mechanisms including cell survival, recovery, differentiation, induction of quiescence, among others.

TEM structure 100 may also be used to evaluate the use of cryosurgical or other ablative techniques and the molecular responses of cells to those techniques. TEM structure 100 provides for a more in vivo-like environment with the ease of use and assessment capabilities of an in vitro system. TEM structure 100 may further be used for three-dimensional (3D) culturing of human cancer cells. In one aspect, TEM structure 100 approximates an actual tissue (with or without simulated vasculature). In turn, deciphering these cells' cellular responses to various treatment modalities facilitates evaluation over a temperature gradient as well as at set, end point temperatures to compare with monolayer cultures.

TEM structure 100 may also be used to create a 3D model of, e.g., prostate cancer cells. By more closely simulating actual in vivo conditions, the use of TEM structure 100 in prostate cancer studies leads to more accurate predictions of cell behavior in response to cryosurgery or other tumor ablative techniques. Mechanisms of cell death, necrosis or apoptosis, can then be evaluated. Further, the TEM construct allows for exploration of biochemical responses of human cancer cells to low temperature insults at levels not possible with standard 2D cultures.

In another use, TEM structure 100 simulates the characteristics of soft tissue, in particular, the tissue characteristics that affect the insertion forces required to introduce a medical device such as a biopsy needle, cryoprobe, or other instrument. In one aspect, TEM stack 103 has a non-homogenous composition to more closely approximate soft tissue. In other embodiments, a homogenous composition may be desired. As such, the matrix 108 (FIG. 8) can be varied to affect the gel solidification and cellular composition that results in a comparable study of actual tissues.

In a further use, TEM structures 100 may be produced and grown in culture to allow for the maturation of the tissue. TEM structures 100 are then placed into short or long term storage (e.g. refrigerated, frozen, ambient, or dry state stasis). This allows for the on demand retrieval, revival and utilization of TEM structures 100. Storage of the TEMs permits large scale production and distribution of the models to researchers and other end users worldwide. The TEM matrices 108 (FIG. 8) may also be dehydrated or frozen to analyze compositions and/or retrieve cellular compositions as desired. In this regard, the tissue matrix may also be cryo-fractured at cryogenic temperatures to separate particles by size. This removes any fraction of moisture that may have been absorbed to give a dry particulate cellular (or acellular) tissue matrix. In such an embodiment, the mechanical damage is reduced such that breaking of the collagen results in a clean break (rather than frayed ends). Electron microscopy verifies representative ends of the collagen fibers.

In another use, TEM structure 100 may provide a monitoring system to detect and test environmental conditions. For example, TEM structure 100 may be used as a living bio-detection or reporter system in settings such as oil and gas exploration/drilling, may be incorporated with select cell types to be used for agent detection in bio-defense, or may be used to monitor air pollutants in factories, cities, and other locations. This concept is generally referred to as a "canary in a coal mine" first line bio-defense system for the detection of toxic conditions, and may supplements current technologies including mass spectroscopy, air monitoring, and Raman spectroscopy for environmental monitoring.

In a further use, TEM structure 100 is used as a training tool to simulate tissue for physicians to practice surgical techniques, develop new procedures, and train on the use of new medical devices. TEM structure 100 allows for assessment of the procedural technique as well as outcome assessment or prediction for each procedure through post-manipulation assessment of the response of the living cellular component of TEM structure 100. TEM structures 100 may also be created and subsequently stored in a liquid, solid, frozen or dry state to allow for TEM storage, banking and shipment allowing for on-demand utilization by an end user.

As used herein, the terms "first," "second," and the like, do not denote any order, quantity, or importance, but rather are used to distinguish one element from another, and the terms "a" and "an" herein do not denote a limitation of quantity, but rather denote the presence of at least one of the referenced item. The modifier "about" used in connection with a quantity is inclusive of the stated value and has the meaning dictated by the context (e.g., includes the degree of error associated with measurement of the particular quantity). The suffix "(s)" as used herein is intended to include both the singular and the plural of the term that it modifies, thereby including one or more of that term (e.g., the metal(s) includes one or more metals). Ranges disclosed herein are inclusive and independently combinable (e.g., ranges of "up to about 25 mm, or, more specifically, about 5 mm to about 20 mm," is inclusive of the endpoints and all intermediate values of the ranges of "about 5 mm to about 25 mm," etc.).

While various embodiments are described herein, it will be appreciated from the specification that various combinations of elements, variations or improvements therein may be made by those skilled in the art, and are within the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A tissue engineered model (TEM) structure, the TEM structure comprising: at least one TEM segment, each TEM segment comprising:
    a first membrane defining a plane;
    a three-dimensional frame disposed on and affixed to the first membrane, wherein the three-dimensional frame includes:
        a band having a first edge affixed to the first membrane, and a height extending from the first edge in a direction that is substantially perpendicular to the plane of the first membrane, to a second edge,
        wherein the band defines a bounded area on the plane of the first membrane, and a volume equal to the bounded area times the height of the band; and
    a matrix disposed within and filling the volume defined within the three-dimensional frame and the first membrane, the matrix comprising solidified gel and cells.

2. The TEM structure of claim 1, wherein the bounded area of each TEM segment has a width in the plane of the first membrane of about 2 cm to about 5 cm, and each TEM segment has a height of about 2 mm to about 8 mm.

3. The TEM structure of claim 1, wherein the solidified gel and cell matrix further comprises:
    a culture medium;
    a gelling agent, wherein the gelling agent comprises collagen; and
    stem cells.

4. The TEM structure of claim 3, wherein each TEM segment contains a first defined region of cells and a second defined region of cells within the TEM segment,
    wherein the first and the second defined regions of cells include a first and a second region of cells disposed in distinct areas within the bounded area.

5. The TEM structure of claim 1, wherein the frame further comprises a groove on an outward facing surface thereof, and
    wherein the TEM segment further comprises an o-ring disposed within the groove for retaining the first membrane in position.

6. The TEM structure of claim 1, wherein the first membrane is optically clear, biologically active, and microporous, and wherein the membrane further comprises a cellulose sheet.

7. The TEM segment of claim 1, wherein the bounded area defined by the frame is substantially circular, and the volume defined within the three-dimensional frame and the first membrane is substantially cylindrical.

8. The TEM structure of claim 6, further comprising a plurality of TEM segments, wherein each of the plurality of TEM segments is vertically stacked and substantially horizontally aligned with each other TEM segment, such that the second edge of the first TEM segment is adjacent to the first edge of the second TEM segment, and wherein the upper surface of the solidified gel and cell matrix of the first TEM segment contacts the lower surface of the first membrane of the second TEM segment, forming an engineered tissue that is substantially continuous between the first TEM segment and the second TEM segment.

9. The TEM structure of claim 8, wherein the plurality of TEM segments further comprises between about two TEM segments and about fifteen TEM segments.

10. The TEM structure of claim 1, wherein the solidified gel and cell matrix further comprises:
    a) at least one of a culture medium or a salt solution;
    b) a gelling agent, wherein the gelling agent is selected from the group consisting of collagen, matrigel, gelatin, agarose, fibronectin, engineered scaffolds, polymer based gels, hydrogels and a combination thereof; and
    c) a cell type selected from the group consisting of cancerous or normal prostate cells, renal cells, breast cells, pancreatic cells, liver cells, lung cells, neuronal cells, esophageal cells, skin cells, endothelial cells, epithelial cells, smooth muscle cells, cardiomyocytes, stem cells and a combination thereof.

11. The TEM structure of claim 10, wherein the TEM segment contains a heterogeneous mixture of cell types in the solidified gel and cell matrix.

12. The TEM structure of claim 10, wherein the TEM segment contains homogeneous cells in the solidified gel and cell matrix.

13. The TEM structure of claim 3, wherein each TEM segment contains a first defined region of cells and a second defined region of cells within the TEM segment,
   wherein the first and the second defined regions of cells include a first and a second region of cells disposed in distinct areas within the bounded area.

14. The TEM structure of claim 1, wherein the bounded area defined by the frame is substantially ovoid, square, rectangular, or organ-shaped.

15. The TEM structure of claim 1, further comprising a second membrane that is substantially parallel to the first membrane,
   wherein the second membrane is affixed to the second edge of the band such that the matrix is disposed within and fills the volume defined by the three-dimensional frame, the first membrane, and the second membrane.

16. The TEM structure of claim 15, wherein the matrix contacts both the first membrane and the second membrane.

* * * * *